United States Patent [19]

Rosendal

[11] Patent Number: Plant 6,102

[45] Date of Patent: Feb. 9, 1988

[54] EXACUM NAMED WHITE ROSETTE

[75] Inventor: Erik Rosendal, Assens, Denmark

[73] Assignee: Nurserymen's Exchange, San Francisco, Calif.

[21] Appl. No.: 832,912

[22] Filed: Feb. 24, 1986

[51] Int. Cl.[4] ..... A01H 5/00
[52] U.S. Cl. ..... Plt./68
[58] Field of Search ..... Plt./68

*Primary Examiner*—Robert E. Bagwill

*Attorney, Agent, or Firm*—Townsend and Townsend

[57] ABSTRACT

A new and distinct variety of Exacum plant characterized by double flowers, with the normal 5 anthers transformed into a rosette of petals in the center of the flower, floriferousness, blooming habits and the sterility of the flower. Plants can be propagated by asexual processes true to type. Rooting ability of the variety is excellent. The semidouble flower differs from that of the other known cultivars.

2 Drawing Figures

BACKGROUND OF THE NEW PLANT

The present new variety "White Rosette" was discovered by me in a commercial greenhouse in Denmark in 1984 as a spontaneous mutant within a large number of the Exacum Affine Balf. cultivar "Best White" grown as pot plants.

Asexual propagation of my new cultivar by cuttings in my greenhouse through several generations, has proved that the new cultivar is true to type, and constant in its characteristics. Descriptions were carried out on Nov. 12, 1985. Color readings were based on the Royal Horticultural Society's Colour Chart.

DESCRIPTION OF DRAWINGS

The new plant is illustrated in the accompanying drawings in which.

BRIEF SUMMARY

Figure 1:
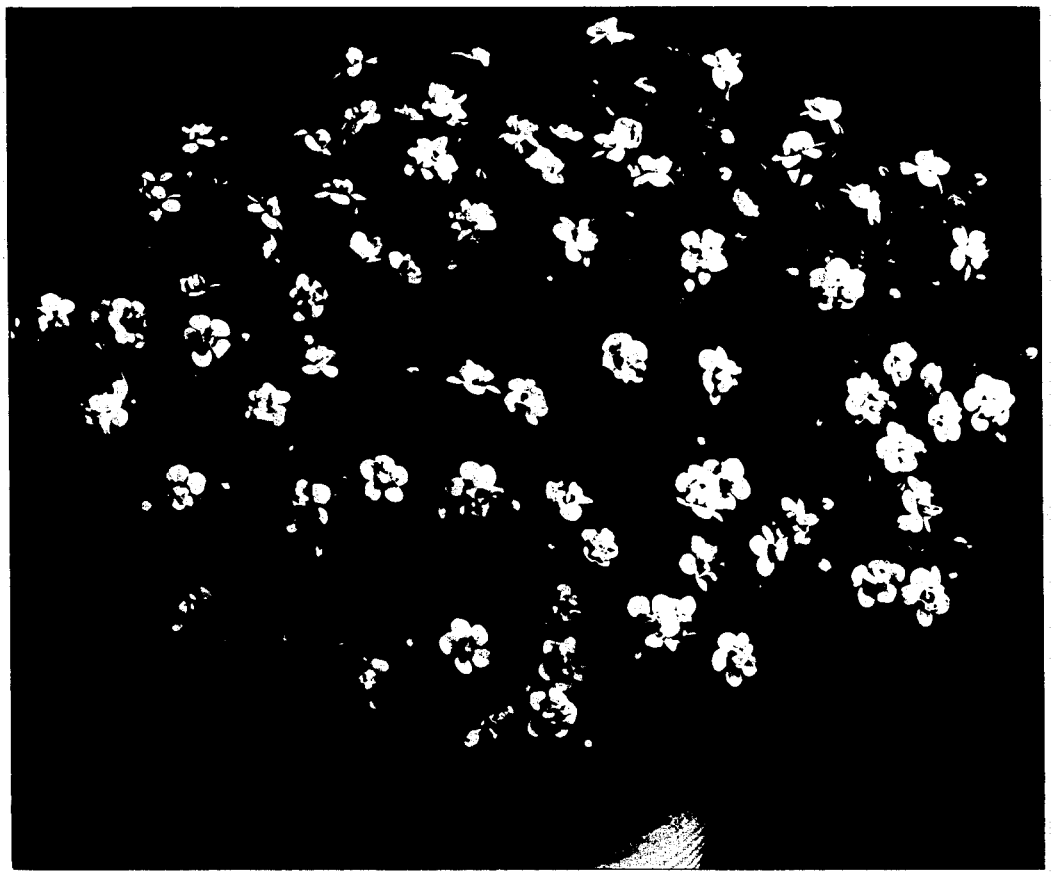
FIG. 1 is a full-color photograph of a potted plant in full bloom.
Figure 2:
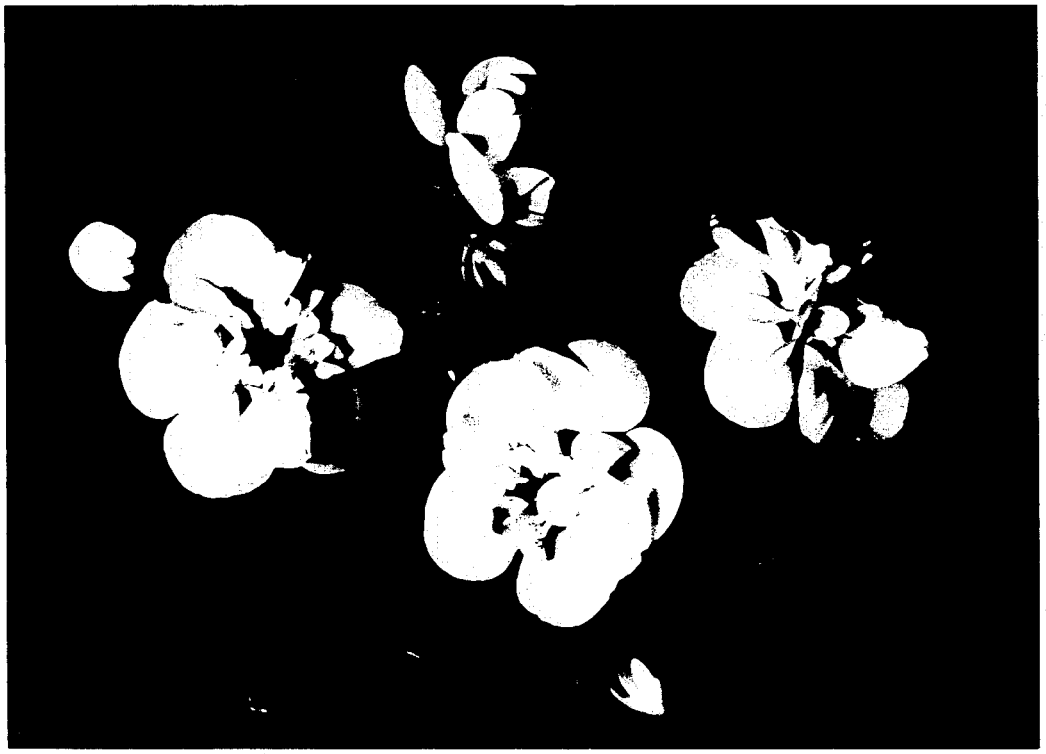
FIG. 2 is a full-color photograph of the blossoms of the plant.

Exacum "White Rosette" is a characteristic new mutant from a known seed propagated cultivar "Best White" and distinguishable from its origin as follows:

1. The flowers are semidouble.
2. Growth rate is equal to single-flowered seed-propagated cultivars.
3. Growth habit as potted plants is compact with an excellent branching ability.
4. Stamens are normally absent as most have become petalloid, forming a rosette in the flower center.
5. The flowers are sterile and produce no seed.
6. Reproduces easily with cuttings.
7. The keepability of the flower is slightly better than that for the single-flowered cultivars.

The accompanying color photograph illustrates the overall appearance of the cultivar "White Rosette." The flower color is white at full maturity, greenish white as a bud. The following is based on observations made on Nov. 12, 1985.

PLANT

Origin: Mutation in a well defined seed-grown cultivar "Best White."

Form: Upright with a distinct dichotomous branching ability right from base to the terminal shoots.
Height: To flowering 18–25 cm.
Plant diameter: Similar to height.
Growth rate: Fast under good light condition.
Type of cutting: Terminal shoots or stem segments.
Rooting time: 12–14 days.
Rooting habit: Fast and dense.

FOLIAGE

Arrangements: Opposite sessile leaves at all nodes.
Shape of leaves: Cordate to elliptic ovate.
Tip: Acute.
Base: Attenuate.
Margin: Entire.
Venation: Faintly three-veined from petiole. Middle vein strongest.
Size: Leaf-blade and petiole 40–55 cm. Length of blade 25–45 mm. Width at widest point 28–40 mm.
Surface: Smooth, with slightly depressed veins.
Texture: Glabrous.
Variegation: None.
Color:
*Petiole.*—144 A.
*Veins.*—144 B.
*Leaf surface.*—137 C, lower side — 143 B.

STEM

Color: Basic color green with shades of purple 183C, at internodes strong purplish tinted.
Length of internodes: 30–40 mm.
Structure: Strong, rounded quadrangular.
Breaking action: Sympodial. Flowers solitary in dichasia. Each node with two lateral shoots.

FLOWER

Form: Round.
Born: Solitary, terminal in dichasia.
Bud: Round, 4–5 mm. in diameter. Color 145 B.
Calyx: 5 winged. Color 143 B.
Petals: Five white, outer petals, 8–9 mm. each, forming a round flower, 18–20 mm. in diameter. In the center, 5 incurved, crinkled petals of transformed anthers form a rosette. The number and type of these inner petals depend on the prevailing light conditions. During the summer, the rosette will be tight and have a (Continued on next page.)

diameter of 7–9 mm. In the winter, some anthers will only be partly petalloid or form sterile anthers.

Style: 12 mm. long, white, bent with greenish stigma.

Stamens: Normally absent.

Petal color: White with a greenish base, lower side 149 D at base.

Lasting quality: Average keepability one week depending on temperature.

Behaviour: The large number of flowers appear as an eye catcher at the surface of the compact green foliage, where new buds and flowers succeed.

Pedicels: 15–25 mm., purplish green.

Having thus disclosed my invention, I claim:

1. "White Rosette" to be a new and distinct cultivar of Exacum as shown and described, characterized by its semidouble white flowers, with the normal five anthers transformed into a rosette of petals in the center of the flower, its floriferousness, its blooming habits, by the sterility of the flower with the plants being propagated by asexual processes true to type, excellent rooting ability and the semidouble flower differing from that of the other known cultivars.

* * * * *